(12) United States Patent
Carney

(10) Patent No.: US 8,790,324 B2
(45) Date of Patent: Jul. 29, 2014

(54) SIDE PANELS FOR AN ABSORBENT ARTICLE

(75) Inventor: Joshua Carney, Philadelphia, PA (US)

(73) Assignee: SCA Hygiene Products AB, Gothenburg (SE)

( * ) Notice: Subject to any disclaimer, the term of this patent is extended or adjusted under 35 U.S.C. 154(b) by 476 days.

(21) Appl. No.: 12/789,569

(22) Filed: May 28, 2010

(65) Prior Publication Data

US 2011/0295224 A1 Dec. 1, 2011

(51) Int. Cl.
*A61F 13/15* (2006.01)

(52) U.S. Cl.
USPC ...... 604/385.03; 604/386; 604/387; 604/396; 604/385.24

(58) Field of Classification Search
USPC ........... 604/385.03, 386, 387, 396, 385.24
See application file for complete search history.

(56) References Cited

U.S. PATENT DOCUMENTS

| | | | |
|---|---|---|---|
| 5,358,500 A | * | 10/1994 | Lavon et al. ............ 604/385.29 |
| 5,386,595 A | | 2/1995 | Kuen et al. |
| 5,669,897 A | | 9/1997 | Lavon et al. |
| 2008/0004590 A1 | * | 1/2008 | Lodge et al. .............. 604/396 |

FOREIGN PATENT DOCUMENTS

| | | |
|---|---|---|
| DE | 93 21 556 UI | 9/1999 |
| EP | 0617941 | 10/1994 |
| EP | 1350493 | 3/2008 |
| FR | 2 585 217 | 1/1987 |
| WO | WO 91/08725 | 6/1991 |
| WO | 2009/057006 | 5/2009 |

* cited by examiner

*Primary Examiner* — Jacqueline F. Stephens
(74) *Attorney, Agent, or Firm* — Drinker Biddle & Reath LLP

(57) ABSTRACT

An absorbent article includes side panels for securing around the waist of the user. The absorbent article includes a first end, a second end, and an absorbent section therebetween. The first end has longitudinal side edges and a first waist line edge. A pair of side panels extend from longitudinal side edges of said first end of the absorbent article, and are shaped and dimensioned so as extend beyond the first waist line edge of the first end of the absorbent article a longitudinal extent so that the side panels may be secured above the hip joints of the user.

27 Claims, 14 Drawing Sheets

SIDE PANELS FOR AN ABSORBENT ARTICLE

FIELD OF THE INVENTION

The present invention relates to side panels for an absorbent article. More particularly, the present invention relates to side panels for an absorbent article to better secure the absorbent article around the waist of a user.

BACKGROUND OF THE INVENTION

Absorbent articles in the form of disposable diapers and incontinence briefs are generally known in which the absorbent article is provided with a fastening system including a pair of side panels with fastening tabs secured to both sides of one end region of the absorbent article. The fastening tabs are intended to engage receiving means located on the other end region of the absorbent article. Such an absorbent article is generally placed around the waist of a user.

For example, with reference to FIG. 1, a prior art absorbent article 2 includes two side panels 4 secured to the front end 6 of the absorbent article 2. As shown in FIG. 1, the side panels 4 are designed to be secured at the hip joint of a user. However, when a user walks, the load angle changes, thereby wiggling the hooks free from the nonwoven. This causes the article to slip off the user.

EP 0 617 941 discloses a garment with an attachment system. The attachment system includes narrow strap members 40 that bridge over the sides of the product. The straps are releasably secured to the front and back ends of the product via two different fastener types, with small or fixed fastening areas. As such, a product that is fastened to a smaller individual may be loosely fastened and risk falling off, while a product fastened to a larger person may be very tight. In both cases, the forces that are taken up the straps will be loaded onto a small area for the wearer and thus tend to dig into the skin. In addition, because the forces will be loaded on a small area, there is a greater risk that the straps will move up and down with the movement of the wearer.

WO 2009/057006 discloses a product that is designed to sit very low on the wearer. The fasteners are positioned along the groins of the wearer, an area of the body which moves a lot when a person is moving. As such, there is a large risk of chafing the skin.

Accordingly, there is a need in the art to provide an absorbent article that can be secured in a manner to prevent the product from slipping off a user.

SUMMARY

According to a first aspect of the invention, an absorbent article comprises a first end, a second end, and an absorbent section therebetween. The first end has longitudinal side edges and a first waist line edge. A pair of side panels extend from longitudinal side edges of the first end of the absorbent article. The pair of side panels are fixedly secured to or integral with the longitudinal side edges of the first end of the absorbent article. The side panels are shaped and dimensioned so as extend beyond the first waist line edge of the first end of the absorbent article a longitudinal extent so that the side panels may be secured above the hip joints of the user.

According to a second aspect of the invention, an absorbent article comprises a first end, a second end, and an absorbent section therebetween. The first end has longitudinal side edges and a first waist line edge. A pair of side panels extend from longitudinal side edges of the first end of the absorbent article. The side panels are fixedly secured to or integral with the longitudinal side edges of the first end of the absorbent article. The side panels include a first edge, said first edge extending beyond the first waist edge line, wherein an angle between a line drawn tangent to the first edge and a line extending along the first waist line edge ranges between about 10-90°.

Yet another feature of the present invention is that the longitudinal extent of the side panels from the first waist line edge to a distal end of the side panel is preferably between about 3-15% of the longitudinal extent of the article. These further features apply to each of the two aspects described above.

Yet a further feature of the present invention is that the a longitudinal extent of the article is about between 700 mm to about 1800 mm and the longitudinal extent of the side panels from first waist line edge to a distal end of the side panel is between about 21 mm to about 270 mm. These further features apply to each of the two aspects described above.

Yet another feature of the present invention is that wherein a longitudinal extent of the article is about between 200 mm to about 500 mm and the longitudinal extent of the side panels from the first waist line edge to a distal end of the side panel is between about 6 mm to about 75 mm. These further features apply to each of the two aspects described above.

Still further another feature of the present invention is that the side panels include a first edge, said first edge extending beyond the first waist edge line, wherein an angle between a line drawn tangent to the first edge and a line extending along the first waist line edge ranges between about 10-90°, more preferably between about 30-90°, and most preferably between about 35-55°. These further features apply to each of the two aspects described above.

Yet another feature of the present invention is that a longitudinal extent of the article is about between 700 mm to about 1800 mm and the side panels have a longitudinal length ranging between about 84 mm and 360 mm and a transverse width ranging between about 70 mm and 540 mm. These further features apply to each of the two aspects described above.

Still a further feature is that the longitudinal length of the side panels range between about 12-20% of the longitudinal length of the article L1 and a transverse width of the panels L2 ranging between about 10-30% of the longitudinal length of the article L1. These further features apply to each of the two aspects described above.

Still yet another feature of the present invention is that a longitudinal extent of the article is about between 200 mm to about 500 mm, the side panels having a longitudinal length ranging between about 24 mm and 100 mm and a transverse width ranging between about 20 mm and 150 mm. These further features apply to each of the two aspects described above.

Still further another feature of the present invention is that each side panel includes a fastening device for securing the first end to the second end of the absorbent article. These further features apply to each of the two aspects described above.

Yet another feature of the present invention is that the side panels include an elastic portion, the elastic portion having an elastic elongation of 20% to 250%. These further features apply to each of the two aspects described above.

Each of the features described above may be taken alone or in any possible combination for an enhanced effect improving the wearability of the absorbent article.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements.

DETAILED DESCRIPTION OF THE PREFERRED EMBODIMENTS

Figure 2:
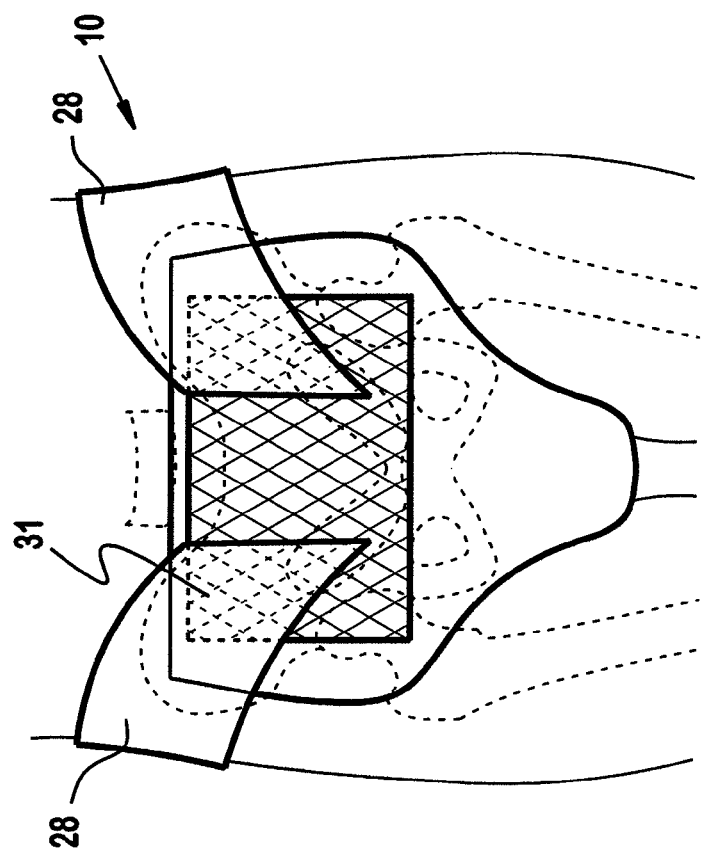
FIG. 2 is a front elevational view of an absorbent article according to the present invention.

The present invention pertains to an absorbent article. An absorbent article is defined as an article or garment used for the absorption of body fluids, including but not limited to, infant diapers, adult incontinence products, and gender specific absorbent products. As known in the art, an absorbent article typically includes a back sheet, a top sheet, and an absorbent core sandwiched therebetween. The preferred embodiments generally illustrate incontinence briefs, i.e., an open type of incontinence article that is worn around the waist of a wearer and that is fastened to the body with the help side panels that bridges that front and the back of the product. If the side panels extend from the back of the product, they wrap around the waist and are fastened to the front of the diaper with fasteners, e.g., hook and loops or adhesive fastening. It should be understood that the present invention pertains to baby articles too.

With reference to FIGS. 2-12, an absorbent article 10 according to features of the present invention is illustrated. With reference in particular to FIGS. 3-12, the absorbent article 10 includes an absorbent section 12, a first end 14 and a second end 16. The first end 14 may be either at a rear or front of the absorbent article 10.

The absorbent article 10 extends in a longitudinal direction and has a length L1. Preferably, the absorbent article 10 has an hour glass shape and includes longitudinal side edges 18, first and second waist line edges 20 and 22, and side edge leg portions 24 and 26. Preferably, the longitudinal extent L1 for an adult absorbent article ranges between about 700 mm to 1800 mm, and for an absorbent article for a child, between about 200 mm to 500 mm.

Figure 3:
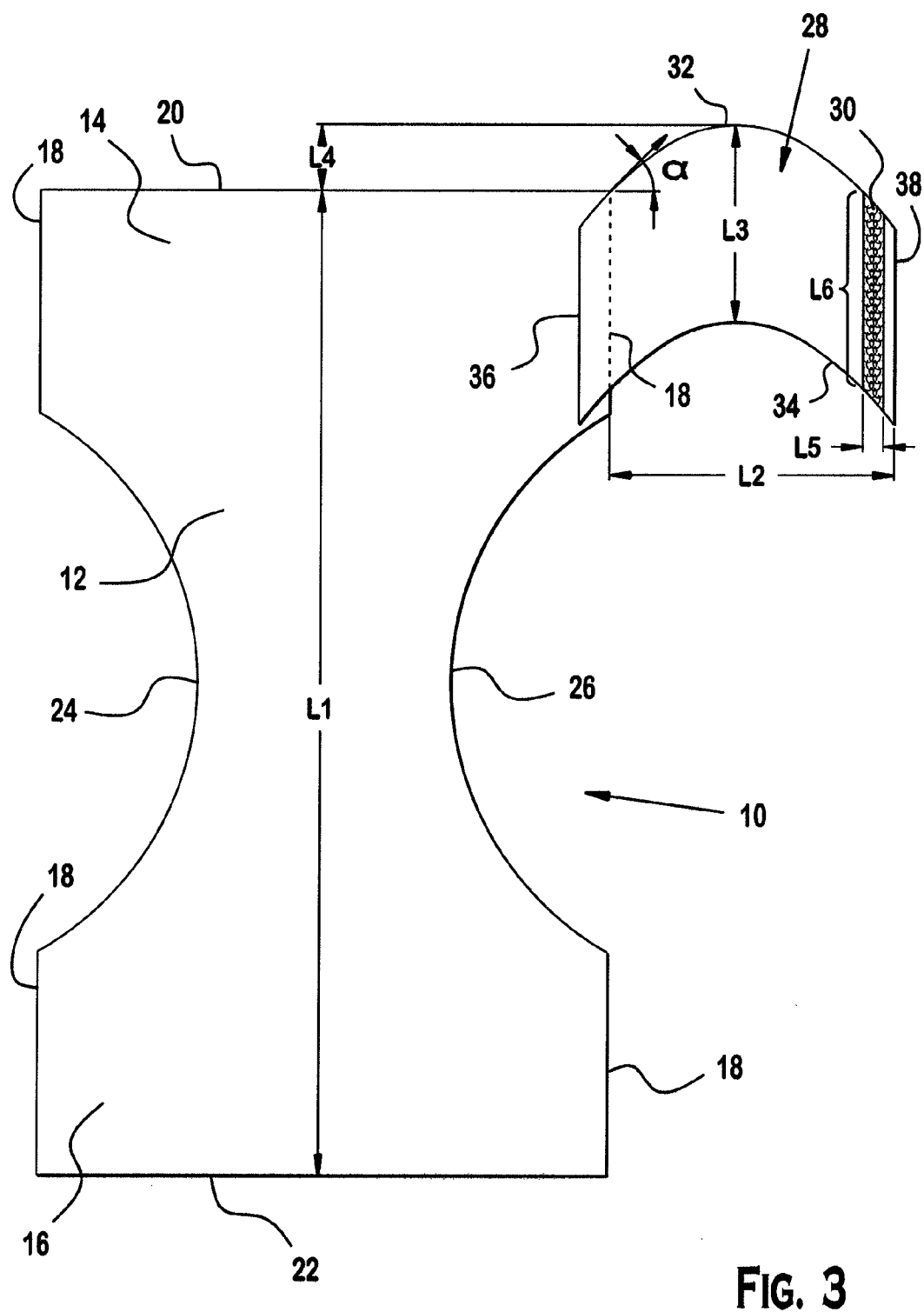
FIG. 3 is a top plan view of a first embodiment of an absorbent article having side panels according to the present invention.

To secure the absorbent article 10 about the user, a pair of side panels are provided. A first embodiment of the side panels 28 are shown in FIG. 3. With reference to FIG. 3, a side panel 28 extends from each longitudinal side edge 18 of the first end 14 of the absorbent article 10. While FIG. 3 only shows one side panel 28, it should be understood that an additional side panel would also extend from the other longitudinal side edge 18 of the first end 14.

A fastening device 30 is provided for securing the first end 14 of the absorbent article 10 to the second end 16 of the absorbent article 10. Preferably, the fastening device 30 is a strip of hook elements which can either be secured directly to the second end 16 or to a loop strip 31 arranged on the second end 16, as shown, for example, in FIG. 2. However, it should be understood that other types of fastening devices are possible, including but not limited to, adhesive, pressure buttons, buttons and button holes, knots, and strings. It should also be understood that the fastening device 30 may be a loop arrangement for securing to a corresponding hook arrangement on the second end 16 of the absorbent article 10.

In addition, while the fastening device 30 is shown at the distal end of the side panel 28, it should be understood that it may be placed at any location and include one or more fastening areas depending on application and design preference. Preferably, hooks are used as the fastening device, and have a width L5 between about 25 mm to about 50 mm and a length L6 that can be 60% of the height of the side panels and that more preferably can be of substantially the same length as L3.

As shown in FIG. 3, the side panel 28 includes a first edge 32, a second edge 34, a proximate edge 36 and a distal edge 38. Preferably, the proximate edge 36 is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels may be integral with the longitudinal side edges 18. That is, the side panels 28 are not fastened to the longitudinal side edges 18, but are made of the same material web as the absorbent article 10.

Preferably, the first edge 32 and second edge 34 are shaped as an arc, and are spaced by a longitudinal length L3. Preferably, the length L3 ranges between about 84 mm to about 360 mm in adult sized products and between about 24 mm to about 100 mm in child sized products. In addition, an angle α between a line drawn tangent to the first edge 32 and a line extending along the first waist line edge 20 ranges between about 10-90°, more preferably between about 30-90°, and most preferably between about 35-55°. The transverse width L2 of the product from the longitudinal side edge 18 of the front end 14 to the distal edge 38 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 28 extends a longitudinal extent L4 from the first waist line edge 20 so that the side panels 28 may be secured at a higher location on the user, as shown for example in FIG. 2. Preferably, the longitudinal extent L4 of side panel 28 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

As such, the side panels 28 extend sufficiently above the waist line of the user so that the article may be secured above the hip bones of a user. In this way, the side panels act like a suspension bridge, thereby avoiding the forces that are exerted by the movements in the hip area when a person walks or moves, e.g. by sitting down. As such, the variable load is controlled by moving the side panel above the hip joint. Also, adding a more even load on the elastic material reduces the torque placed on the hook.

Moreover, the curved side panels 28 allow for the absorbent article 10 to be worn higher on the hip area, above the hip joint, to thereby prevent the article from slipping down due to the movements made by the wearer. This is accomplished by not making the product longer. This helps with the fit and security of the absorbent article. Also, it would allow for the hooks to be loaded in a more secure fashion.

The side panels may be made from the same material as the backsheet, such as, for example, a spun bound, SMS, hydroentangled, carded, latex bounded or heat treated material. Preferably, the material is a nonwoven material with a low basis weight, preferably between 30 and 80 g/m$^2$. Examples of the stretch material are OPTIFLEX 343-100 manufactured by Golden Phoenix Fiberwebs Inc. and FABRIFLEX 309 manufactured by Tredegar Film Products Corp. Examples of non-woven materials include SpunBond material manufactured by PGI Products and Avgol Nonwoven Industries.

Figure 4:
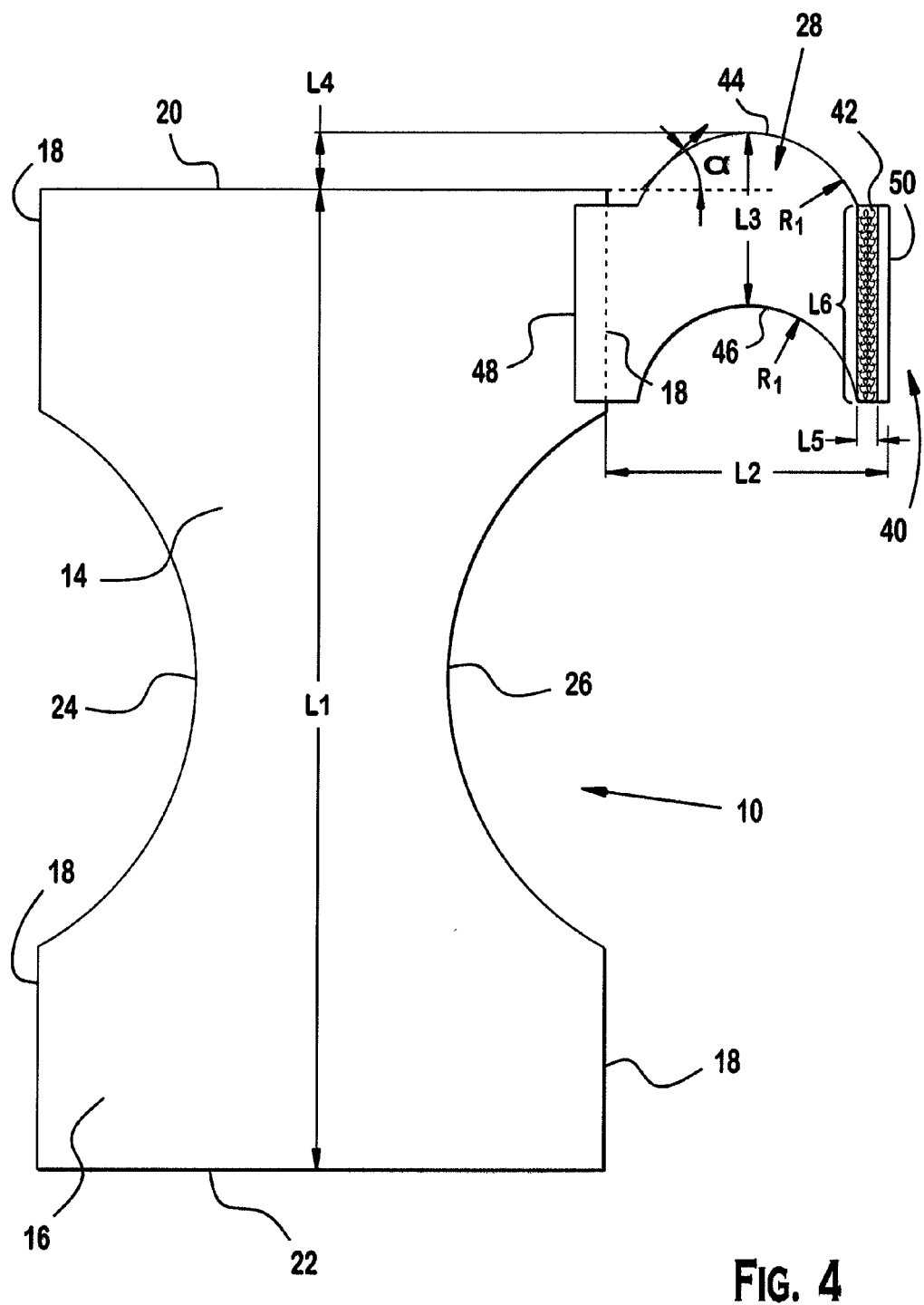
FIG. 4 is a top plan view of a second embodiment of an absorbent article having side panels according to the present invention.

A second embodiment of the side panels 40 on an absorbent article 10 is shown in FIG. 4. A side panel 40 extends from each longitudinal side edge 18 of the first end 14 of the absorbent article 10. While FIG. 4 only shows one side panel 40, it should be understood that an additional side panel would also extend from the other longitudinal side edge 18 of the first end 14.

A fastening device 42 is provided for securing the first end 14 of the absorbent article 10 to the second end 16 of the absorbent article 10. Preferably, the fastening device 42 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 42 may be a loop arrangement for securing to a corresponding hook arrangement on the second end 16 of the absorbent article 10.

In addition, while the fastening device 42 is shown at the distal end of the side panel 40, it should be understood that it may be placed at any location and include one or more fastening areas depending on application and design preference. Preferably, hooks are used as the fastening device, and have a width L5 between about 25 mm to about 50 mm and a length L6 that can be 60% of the height of the side panels and that more preferably can be of substantially the same length as L3.

As shown in FIG. 4, the side panel 40 includes a first edge 44, a second edge 46, a proximate edge 48 and a distal edge 50. Preferably, the proximate edge 48 is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels may be integral with the longitudinal side edges 18. That is, the side panels 28 are not fastened to the longitudinal side edges 18, but are made of the same material web as the absorbent article 10.

Figure 5:
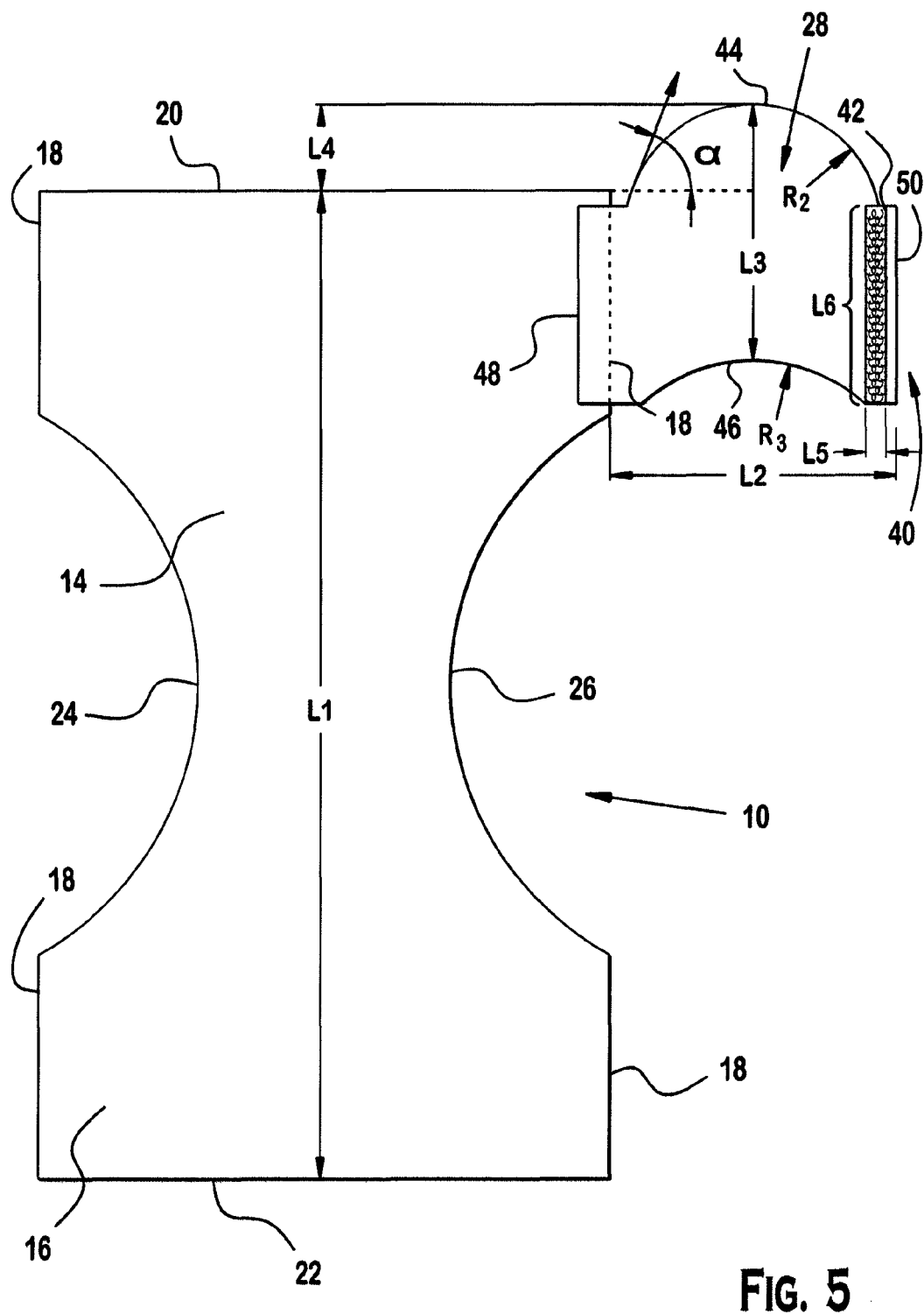
FIG. 5 is a top plan view of a third embodiment of an absorbent article having side panels according to the present invention.

Preferably, the first edge 44 and second edge 46 are shaped as an arc having the same radius of curvature $R_1$. However, the radius of curvature of the first edge 44 and second edge 46 may be different, as shown, for example, in third embodiment illustrated in FIG. 5. FIG. 5 is a similar version of the side panel 40, except that the first edge 44 has a radius of curvature R2 and the second edge 46 has a radius of curvature R3.

With respect to both embodiments of FIGS. 4 and 5, the first edge 44 and second edge 46 are spaced by a length L3. Preferably, the length L3 ranges between about 84 mm to about 360 mm in adult sized products and between about 24 mm to about 100 mm in child sized products. In addition, an angle α between a line drawn tangent to the first edge 44 and a line extending along the first waist line edge ranges between about 10-90°, more preferably between about 30-90°, and most preferably between about 35-55°. The transverse width L2 of the product from the longitudinal side edge 18 of the front end 14 to the distal edge 38 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 40 extends a longitudinal extent L4 from the first waist line edge 20 so that the side panels 40 may be secured at a higher location on the user, as shown for example in FIG. 2. Preferably, the longitudinal extent L4 of side panel 40 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 6:
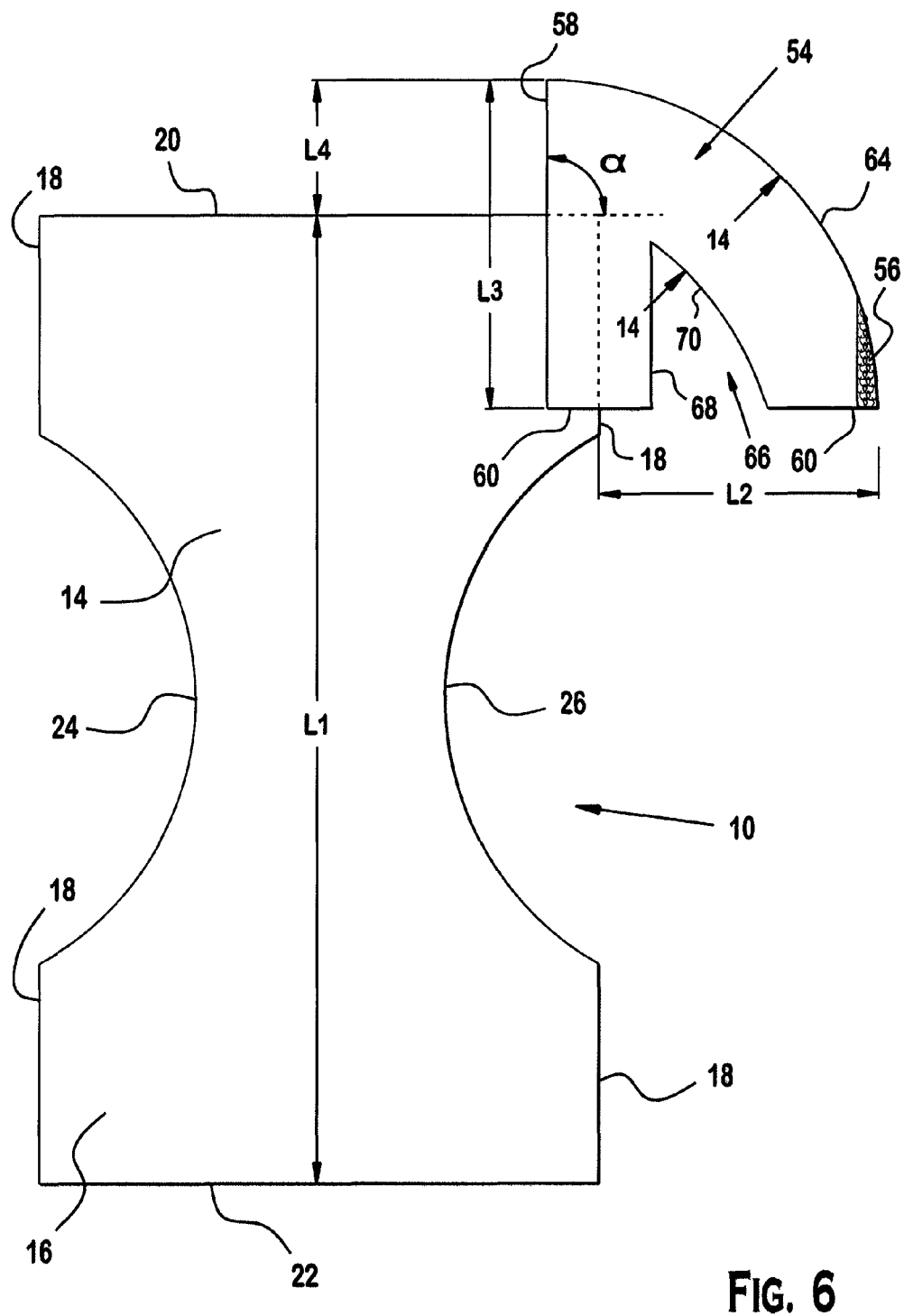
FIG. 6 is a top plan view of a fourth embodiment of an absorbent article having side panels according to the present invention.

A fourth embodiment of the side panels 54 on an absorbent article 10 is shown in FIG. 6. A side panel 54 extends from each longitudinal side edge 18 of the first end 14 of the absorbent article 10. While FIG. 6 only shows one side panel 54, it should be understood that an additional side panel would also extend from the other longitudinal side edge 18 of the first end 14.

A fastening device 56 is provided for securing the first end 14 of the absorbent article 10 to the second end 16 of the absorbent article 10. Preferably, the fastening device 56 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 56 may be a loop arrangement for securing to a corresponding hook arrangement on the second end 16 of the absorbent article 10.

In addition, while the fastening device 56 is shown at the distal end of the side panel 54, it should be understood that it may be placed at any location and include one or more fastening areas depending on application and design preference. Preferably, hooks are used as the fastening device, and have a width L5 between about 25 mm to about 50 mm and a length L6 that can be 60% of the height of the side panels and that more preferably can be of substantially the same length as L3.

As shown in FIG. 6, the side panel 54 includes a first edge 58, second edges 60, and a distal edge 64. Preferably, the first edge 58 is also the proximal edge, which is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels may be integral with the longitudinal side edges 18. That is, the side panels 28 are not fastened to the longitudinal side edges 18, but are made of the same material web as the absorbent article 10

Between the second edges 60 is a cut-out portion 66. Preferably, the cutout portion 66 forms two cut-out edges 68, 70. Cut out edge 70 is curved and preferably has the same radius of curvature R4 as the distal edge 64. In this way, the distal edge 64 acts as a tab to direct the user to grab the side panel therein for affixing to the second end 16.

Preferably, a distance between the top of the first edge 58 and the second edges 60 is a length L3, which ranges between about 84 mm to about 360 mm in adult sized products and between about 24 mm to about 100 mm in child sized products. In addition, an angle $\alpha$ between a line drawn tangent to the first edge 58 and a line extending along the first waist line edge 20 ranges between about 10-90°, more preferably between about 30-90°, and most preferably between about 35-55°. The transverse width L2 of the product from the longitudinal side edge 18 of the front end 14 to the furthest point of distal edge 64 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 54 extends a longitudinal extent L4 from the first waist line edge 20 so that the side panels 54 may be secured at a higher location on the user, as shown for example in FIG. 2. Preferably, the longitudinal extent L4 of side panel 54 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 7:
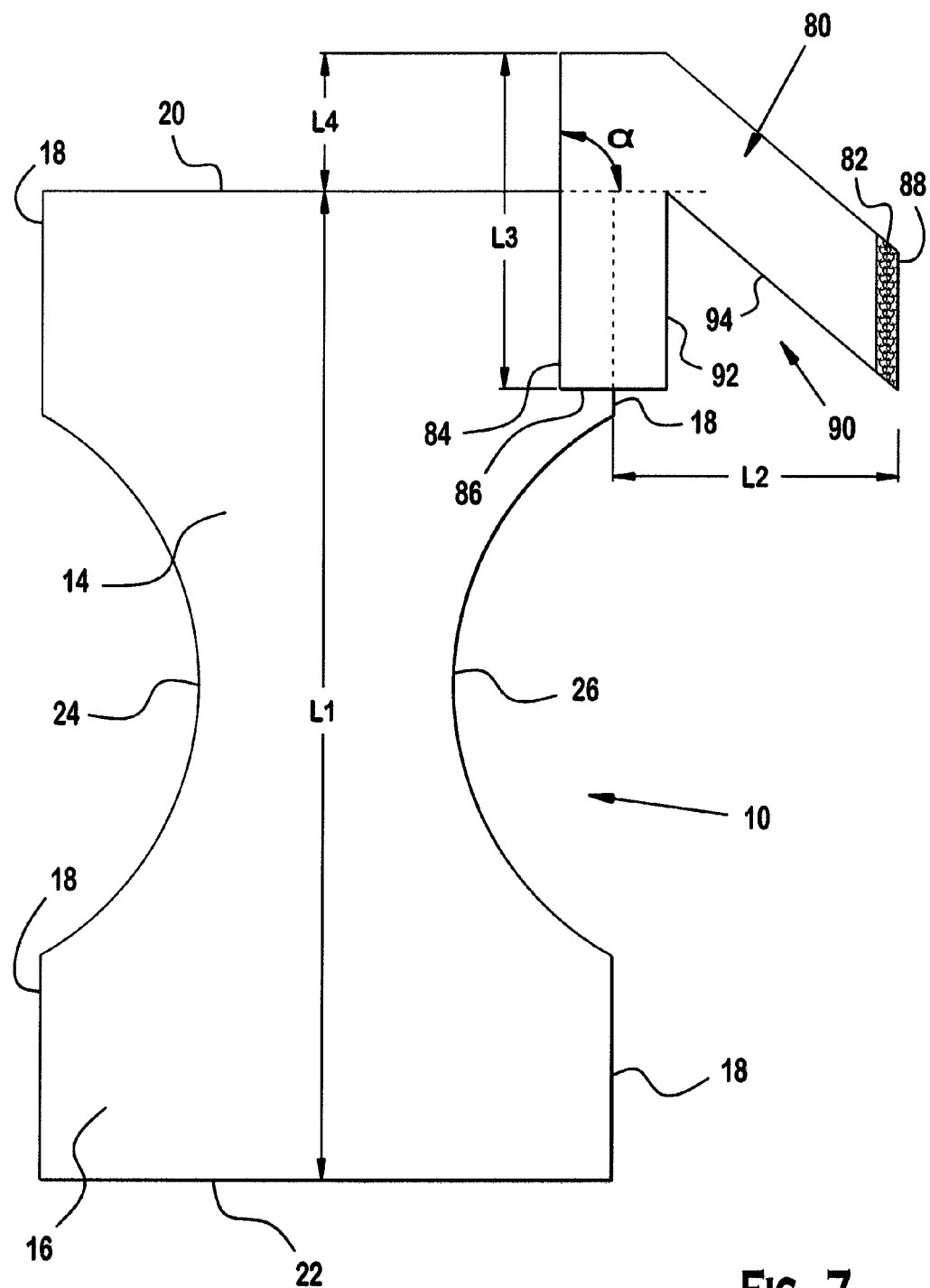
FIG. 7 is a top plan view of a fifth embodiment of an absorbent article having side panels according to the present invention.

A fifth embodiment of the side panels 80 on an absorbent article 10 is shown in FIG. 7. A side panel 80 extends from each longitudinal side edge 18 of the first end 14 of the absorbent article 10. While FIG. 7 only shows one side panel 80, it should be understood that an additional side panel would also extend from the other longitudinal side edge 18 of the first end 14.

A fastening device 82 is provided for securing the first end 14 of the absorbent article 10 to the second end 16 of the absorbent article 10. Preferably, the fastening device 82 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 82 may be a loop arrangement for securing to a corresponding hook arrangement on the second end 16 of the absorbent article 10.

In addition, while the fastening device 82 is shown at the distal end of the side panel 80, it should be understood that it may be placed at any location and include one or more fastening areas depending on application and design preference. Preferably, hooks are used as the fastening device, and have a width L5 between about 25 mm to about 50 mm and a length L6 that can be 60% of the height of the side panels and that more preferably can be of substantially the same length as L3.

As shown in FIG. 7, the side panel 80 includes a first edge 84, second edge 86, and a distal edge 88. Preferably, the first edge 84 is also the proximal edge, which is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels 28 may be integral with the longitudinal side edges 18. That is, the side panels 28 are not fastened to the longitudinal side edges 18, but are made of the same material web as the absorbent article 10

Preferably, a distance between the top of the first edge 84 and the second edge 86 is a length L3, which ranges between about 84 mm to about 360 mm in adult sized products and between about 24 mm to about 100 mm in child sized products. In addition, an angle $\alpha$ between a line drawn tangent to the first edge 84 and a line extending along the first waist line edge 20 ranges between about 10-90°, more preferably between about 30-90°, and most preferably between about 35-55°. The transverse width L2 of the product from the longitudinal side edge 18 of the front end 14 to the furthest point of distal edge 88 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

At the lower end of the side panel 80, there is a cut-out portion 90. Preferably, the cutout portion 90 forms two cut-out edges 92, 94. Cut out edges 92, 94 are shown as being straight, but may be any shape. The cut-out portion 90 isolates the distal edge 88, so that it more clearly acts as a tab to direct the user to grab the side panel therein for affixing to the second end 16.

The side panel 80 extends a longitudinal extent L4 from the first waist line edge 20 so that the side panels 80 may be secured at a higher location on the user, as shown for example in FIG. 2. Preferably, the longitudinal extent L4 of side panel 80 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 8:
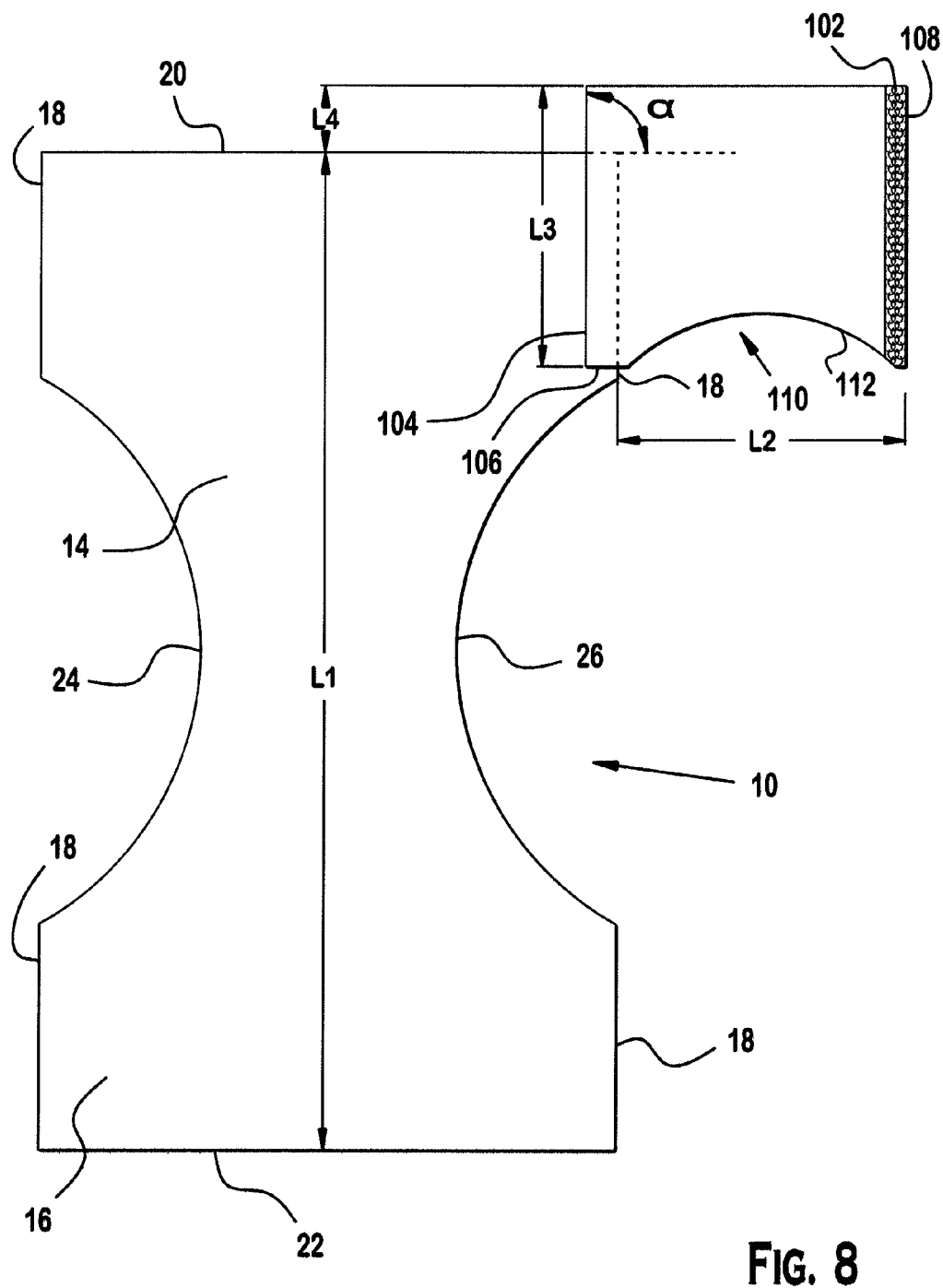
FIG. 8 is a top plan view of a sixth embodiment of an absorbent article having side panels according to the present invention.

A sixth embodiment of the side panels 100 on an absorbent article 10 is shown in FIG. 8. A side panel 100 extends from each longitudinal side edge 18 of the first end 14 of the absorbent article 10. While FIG. 8 only shows one side panel 100, it should be understood that an additional side panel would also extend from the other longitudinal side edge 18 of the first end 14.

A fastening device 102 is provided for securing the first end 14 of the absorbent article 10 to the second end 16 of the absorbent article 10. Preferably, the fastening device 102 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 102 may be a loop arrangement for securing to a corresponding hook arrangement on the second end 16 of the absorbent article 10.

In addition, while the fastening device 102 is shown at the distal end of the side panel 100, it should be understood that it may be placed at any location and include one or more fastening areas depending on application and design preference. Preferably, hooks are used as the fastening device, and range between about 25 mm to about 50 mm. Preferably, hooks are used as the fastening device, and have a width L5 between about 25 mm to about 50 mm and a length L6 that can be 60% of the height of the side panels and that more preferably can be of substantially the same length as L3.

As shown in FIG. 8, the side panel 100 includes a first edge 104, second edge 106, and a distal edge 108. Preferably, the first edge 104 is also the proximal edge, which is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels 28 may be integral with the longitudinal side edges 18. That is, the side panels 28 are not fastened to the longitudinal side edges 18, but are made of the same material web as the absorbent article 10

Preferably, a distance between the top of the first edge 104 and the second edge 106 is a length L3, which ranges between about 84 mm to about 360 mm in adult sized products and between about 24 mm to about 100 mm in child sized products. In addition, an angle α between a line drawn tangent to the first edge 104 and a line extending along the first waist line edge 20 ranges between about 10-90°, more preferably between about 30-90°, and most preferably between about 35-55°. The transverse width L2 of the product from the longitudinal side edge 18 of the front end 14 to the furthest point of distal edge 108 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

At the lower end of the side panel 100, there is a cut-out portion 110. Preferably, the cutout portion 110 forms a cut-out edge 112 which is curved. However, it should be understood that cut-out portion 110 may be any shape. The cut-out portion 110 isolates the distal edge 108, so that it more clearly acts as a tab to direct the user to grab the side panel therein for affixing to the second end 16.

The side panel 100 extends a longitudinal extent L4 from the first waist line edge 20 so that the side panels 108 may be secured at a higher location on the user, as shown for example in FIG. 2. Preferably, the longitudinal extent L4 of side panel 100 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 9:
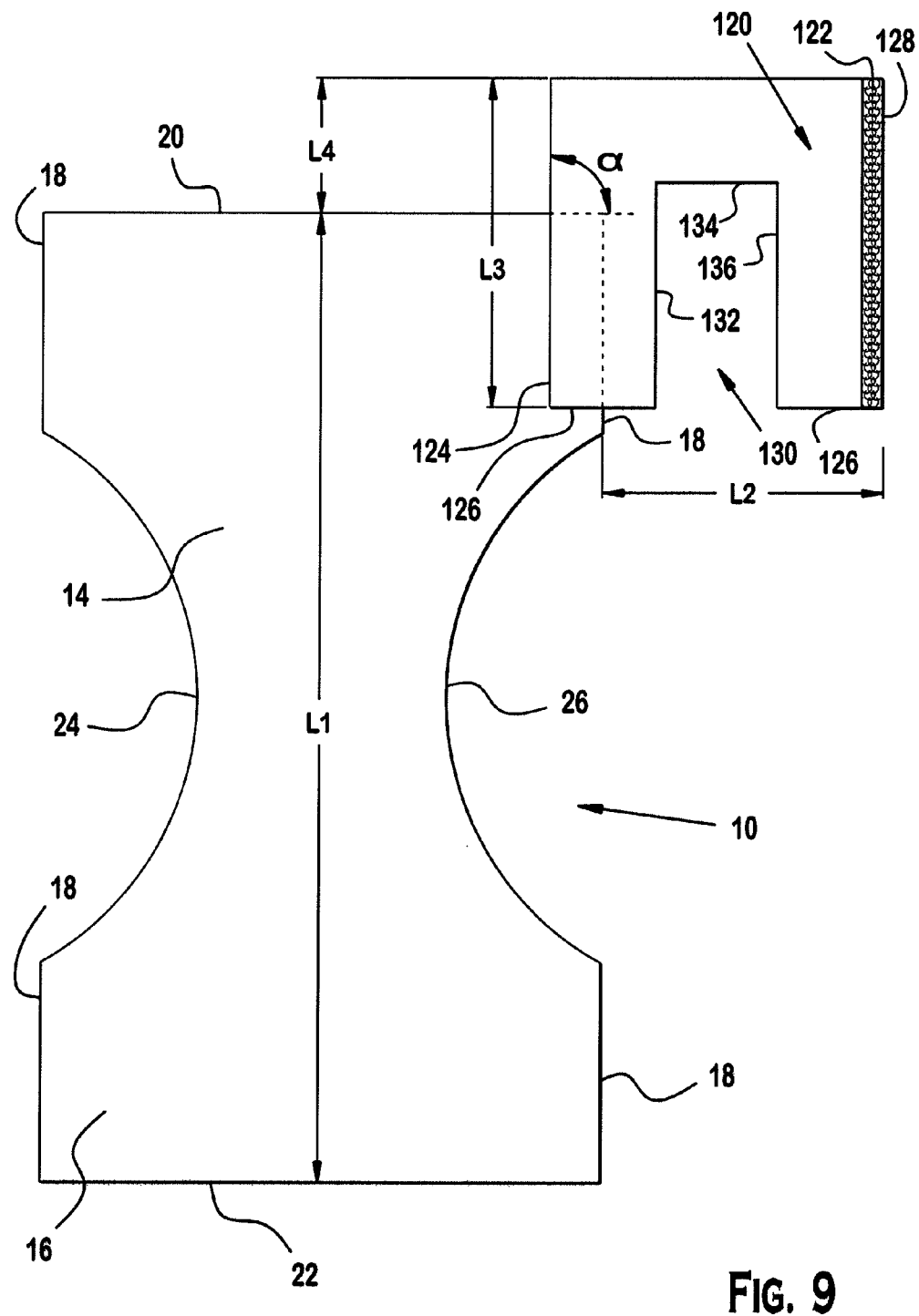
FIG. 9 is a top plan view of a seventh embodiment of an absorbent article having side panels according to the present invention.

A seventh embodiment of the side panels 120 on an absorbent article 10 is shown in FIG. 9. A side panel 120 extends from each longitudinal side edge 18 of the first end 14 of the absorbent article 10. While FIG. 9 only shows one side panel 120, it should be understood that an additional side panel would also extend from the other longitudinal side edge 18 of the first end 14.

A fastening device 122 is provided for securing the first end 14 of the absorbent article 10 to the second end 16 of the absorbent article 10. Preferably, the fastening device 122 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 122 may be a loop arrangement for securing to a corresponding hook arrangement on the second end 16 of the absorbent article 10.

In addition, while the fastening device 122 is shown at the distal end of the side panel 120, it should be understood that it may be placed at any location and include one or more fastening areas depending on application and design preference. Preferably, hooks are used as the fastening device, and range between about 25 mm to about 50 mm. Preferably, hooks are used as the fastening device, and have a width L5 between about 25 mm to about 50 mm and a length L6 that can be 60% of the height of the side panels and that more preferably can be of substantially the same length as L3.

As shown in FIG. 9, the side panel 120 includes a first edge 124, second edge 126, and a distal edge 128. Preferably, the first edge 124 is also the proximal edge, which is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels 28 may be integral with the longitudinal side edges 18. That is, the side panels 28 are not fastened to the longitudinal side edges 18, but are made of the same material web as the absorbent article 10

Preferably, a distance between the top of the first edge 124 and the second edge 126 is a length L3, which ranges between about 84 mm to about 360 mm in adult sized products and between about 24 mm to about 100 mm in child sized products. In addition, an angle α between a line drawn tangent to the first edge 124 and a line extending along the first waist line edge 20 ranges between about 10-90°, more preferably between about 30-90°, and most preferably between about 35-55°. The transverse width L2 of the product from the longitudinal side edge 18 of the front end 14 to the furthest point of distal edge 128 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

At the lower end of the side panel 120, there is a cut-out portion 130. Preferably, the cutout portion 130 forms three cut-out edges 132, 134, and 136. Cut out edges 132, 134, and 136 are shown as being straight, but may be curved or any other shape. The cut-out portion 130 isolates the distal edge 128, so that it more clearly acts as a tab to direct the user to grab the side panel therein for affixing to the second end 16.

The side panel 120 extends a longitudinal extent L4 from the first waist line edge 20 so that the side panels 120 may be secured at a higher location on the user, as shown for example in FIG. 2. Preferably, the longitudinal extent L4 of side panel 120 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 10:
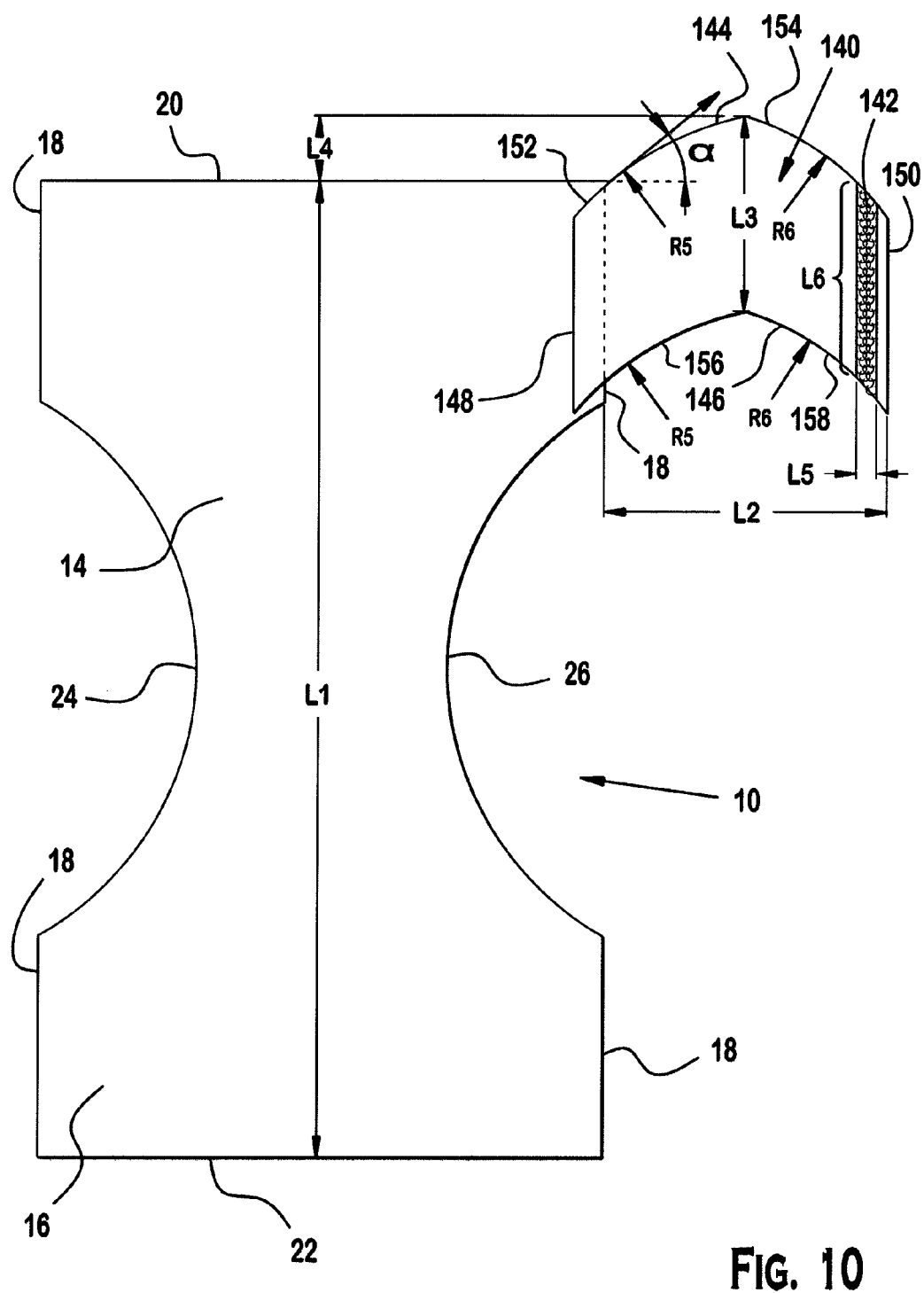
FIG. 10 is a top plan view of a eighth embodiment of an absorbent article having side panels according to the present invention.

A eighth embodiment of the side panels 140 are shown in FIG. 10. With reference to FIG. 10, a side panel 140 extends from each longitudinal side edge 18 of the first end 14 of the absorbent article 10. While FIG. 10 only shows one side panel 140, it should be understood that an additional side panel would also extend from the other longitudinal side edge 18 of the first end 14.

A fastening device 142 is provided for securing the first end 14 of the absorbent article 10 to the second end 16 of the absorbent article 10. Preferably, the fastening device 142 is a strip of hook elements which can either be secured directly to the second end 16 or to a loop strip arranged on the second end 16. However, it should be understood that other types of fastening devices are possible, including but not limited to, adhesive, pressure buttons, buttons and button holes, knots, and strings. It should also be understood that the fastening device 142 may be a loop arrangement for securing to a corresponding hook arrangement on the second end 16 of the absorbent article 10.

In addition, while the fastening device 142 is shown at the distal end of the side panel 140, it should be understood that it may be placed at any location and include one or more fastening areas depending on application and design preference. Preferably, hooks are used as the fastening device, and have a width L5 between about 25 mm to about 50 mm and a length L6 that can be 60% of the height of the side panels and that more preferably can be of substantially the same length as L3.

As shown in FIG. 10, the side panel 140 includes a first edge 144, a second edge 146, a proximate edge 148 and a distal edge 150. Preferably, the proximate edge 148 is secured to the first end 14 of the absorbent article by any means known in the art, e.g., adhesive bonding, welding or ultrasonic welding. The side panel can be fastened either on an inside or an outside surface of the first end or between one or more material layers if the first end is built up from more than one material, e.g. between a topsheet and a backsheet. As such, the side panels 28 may be fixedly secured to the longitudinal side edges 18. Alternatively, the side panels 28 may be integral with the longitudinal side edges 18. That is, the side panels 28 are not fastened to the longitudinal side edges 18, but are made of the same material web as the absorbent article 10.

Preferably, the first edge 144 and the second edge 146 are curved, with varying radii. In particular, first edge 144 includes a first curved portion 152 having a radius of curvature R5 and a second curved portion 154 having a radius of curvature R6. Similarly, the second edge 146 includes a first curved portion 156 having a radius of curvature R5 and a second curved portion 158 having a radium R6. In this way, the first edge 144 and second edge 146 have parallel lines. However, it should be understood that first edge 144 and second edge 146 may be dimensioned and shaped in other ways in accordance with application and design preference. For example, the curved portions 152, 154 of the first edge 154 and the curved portions 156, 158 of the second edge 146 may be straight, waved, or any other configuration in accordance with application and design preference.

The first edge 144 and second edge 146 are spaced by a longitudinal length L3. Preferably, the length L3 ranges between about 84 mm to about 360 mm in adult sized products and between about 24 mm to about 100 mm in child sized products. In addition, an angle α between a line drawn tangent to the first edge 144 and a line extending along the first waist line edge 20 ranges between about 10-90°, more preferably between about 30-90°, and most preferably between about 35-55°. The transverse width L2 of the product from the longitudinal side edge 18 of the front end 14 to the distal edge 150 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 140 extends a longitudinal extent L4 from the first waist line edge 20 so that the side panels 140 may be secured at a higher location on the user, as shown for example in FIG. 2. Preferably, the longitudinal extent L4 of side panel 140 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 11:
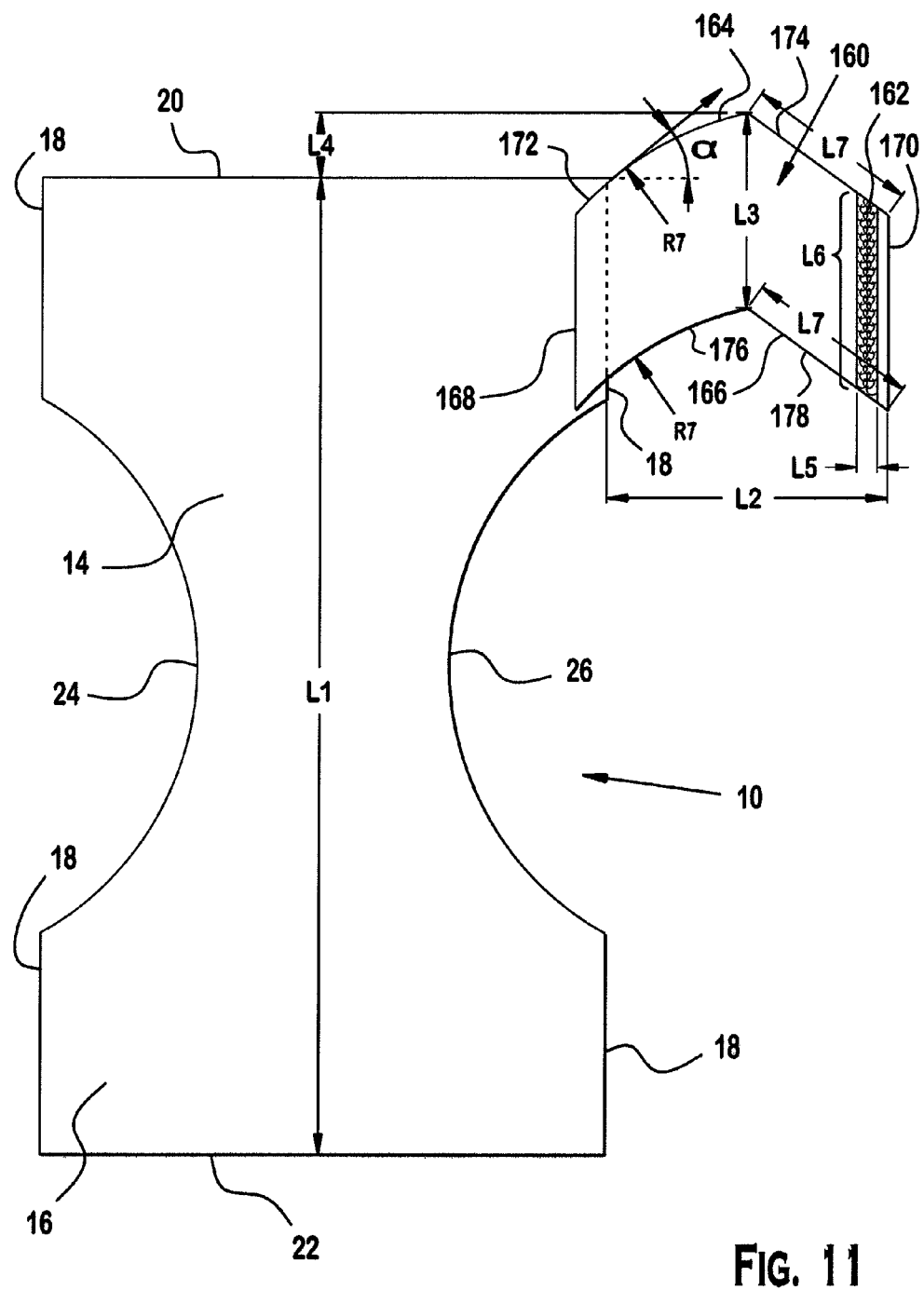
FIG. 11 is a top plan view of a ninth embodiment of an absorbent article having side panels according to the present invention.

For example, FIG. 11 shows a similar panel 160 to the panel 140 described above, which includes a fastening device 162, a first edge 164, a second edge 166, a proximate edge 168 and a distal edge 170. However, the first edge 164 includes a first curved portion 172 having a radius of curvature R7 and a second straight portion 174 having a length L7. Similarly, the second edge 166 includes a first curved portion 176 having a radius of curvature R7 and a second straight portion 178 having a length L7. In this way, the first edge 164 and second edge 166 have curved lines with the same radius of curvature, and straight lines that are parallel. However, it should be understood that the first edge 164 and second edge 166 do not need to be parallel, or equally dimensioned and sized. That is, the first edge 164 and second edge 166 may be dimensioned and shaped in any other way in accordance with application and design preference The first edge 164 and second edge 166 are spaced by a longitudinal length L3. Preferably, the length L3 ranges between about 84 mm to about 360 mm in adult sized products and between about 24 mm to about 100 mm in child sized products. In addition, an angle α between a line drawn tangent to the first edge 164 and a line extending along the first waist line edge 20 ranges between about 10-90°, more preferably between about 30-90°, and most preferably between about 35-55°. The transverse width L2 of the product from the longitudinal side edge 18 of the front end 14 to the distal edge 170 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 160 extends a longitudinal extent L4 from the first waist line edge 20 so that the side panels 160 may be secured at a higher location on the user, as shown for example in FIG. 2. Preferably, the longitudinal extent L4 of side panel 160 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 12:
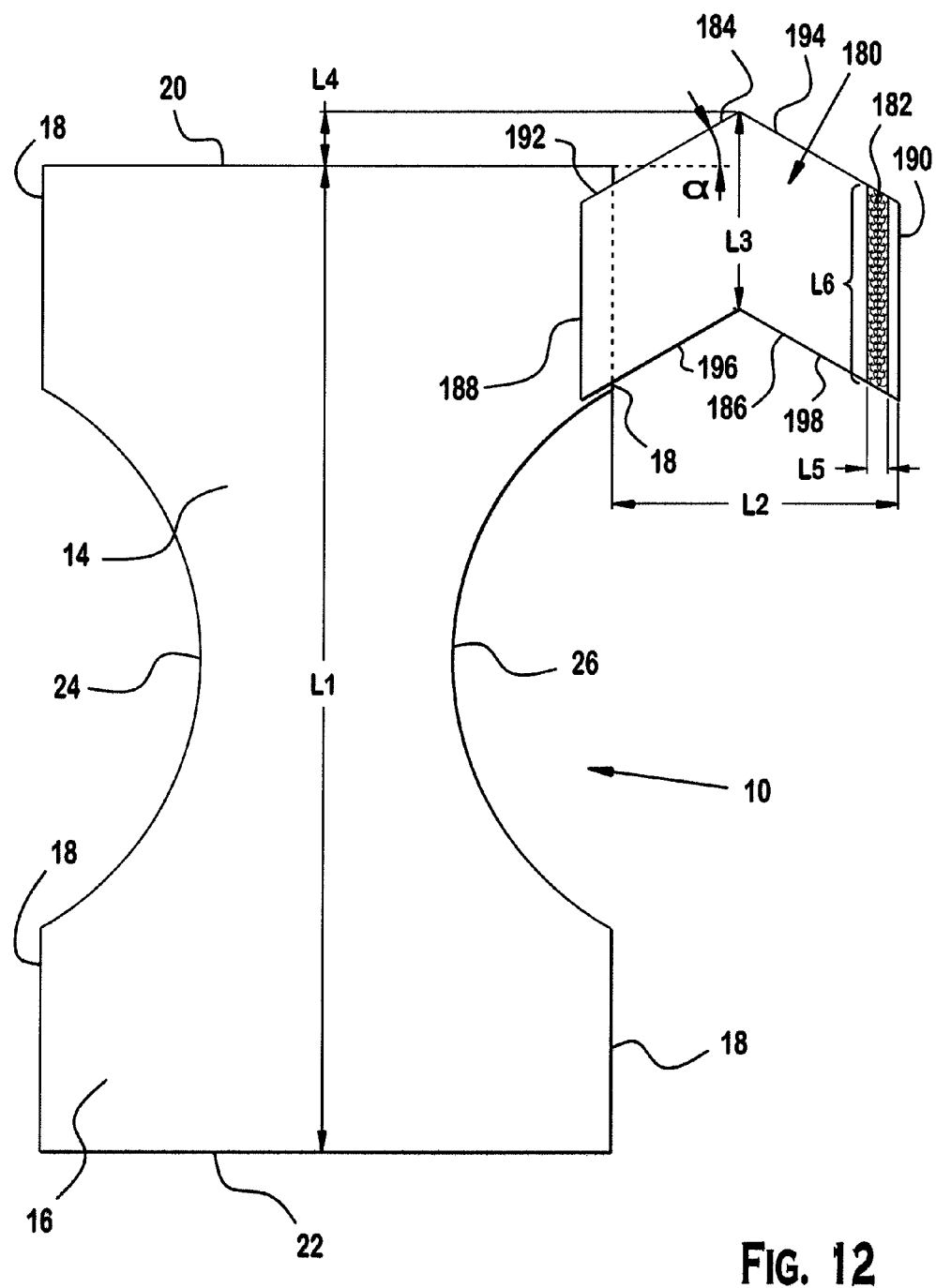
FIG. 12 is a top plan view of a tenth embodiment of an absorbent article having side panels according to the present invention.

For example, FIG. 12 shows a similar panel 180 to the panels 140 and 160 described above, which includes a fastening device 182, a first edge 184, a second edge 186, a proximate edge 188 and a distal edge 190. However, the first edge 184 includes a first straight portion 192 a second straight portion 194. Similarly, the second edge 186 includes a first straight portion 196 and a second straight portion 198. In this way, the first edge 184 and second edge 186 have lines that are parallel. However, it should be understood that the first edge 164 and second edge 166 do not need to be parallel, or equally dimensioned and sized. That is, the first edge 164 and second edge 166 may be dimensioned and shaped in any other way in accordance with application and design preference The first edge 184 and second edge 186 are spaced by a longitudinal length L3. Preferably, the length L3 ranges between about 84 mm to about 360 mm in adult sized products and between about 24 mm to about 100 mm in child sized products. In addition, an angle α between a line drawn tangent to the first edge 184 and a line extending along the first waist line edge 20 ranges between about 10-90°, more preferably between about 30-90°, and most preferably between about 35-55°. The transverse width L2 of the product from the longitudinal side edge 18 of the front end 14 to the distal edge 190 ranges from about 70 mm to about 540 mm in adult sized products and between about 20 mm to about 150 mm in child sized products. Preferably, the longitudinal length of the side panels L3 range between about 12-20% of the longitudinal length of the article L1 and a transverse width of the panels L2 ranging between about 10-30% of the longitudinal length of the article L1.

The side panel 180 extends a longitudinal extent L4 from the first waist line edge 20 so that the side panels 180 may be secured at a higher location on the user, as shown for example in FIG. 2. Preferably, the longitudinal extent L4 of side panel 180 beyond the first waist line edge 20 is between about 21 mm to about 270 mm in an adult sized product and between about 6 mm to about 75 mm in a child sized product. In addition, the longitudinal extent L4 of the side panels from the first waist line edge 20 to a distal end of the side panel 28 is preferably between about 3-15% of the longitudinal extent L1 of the article.

Figure 13:
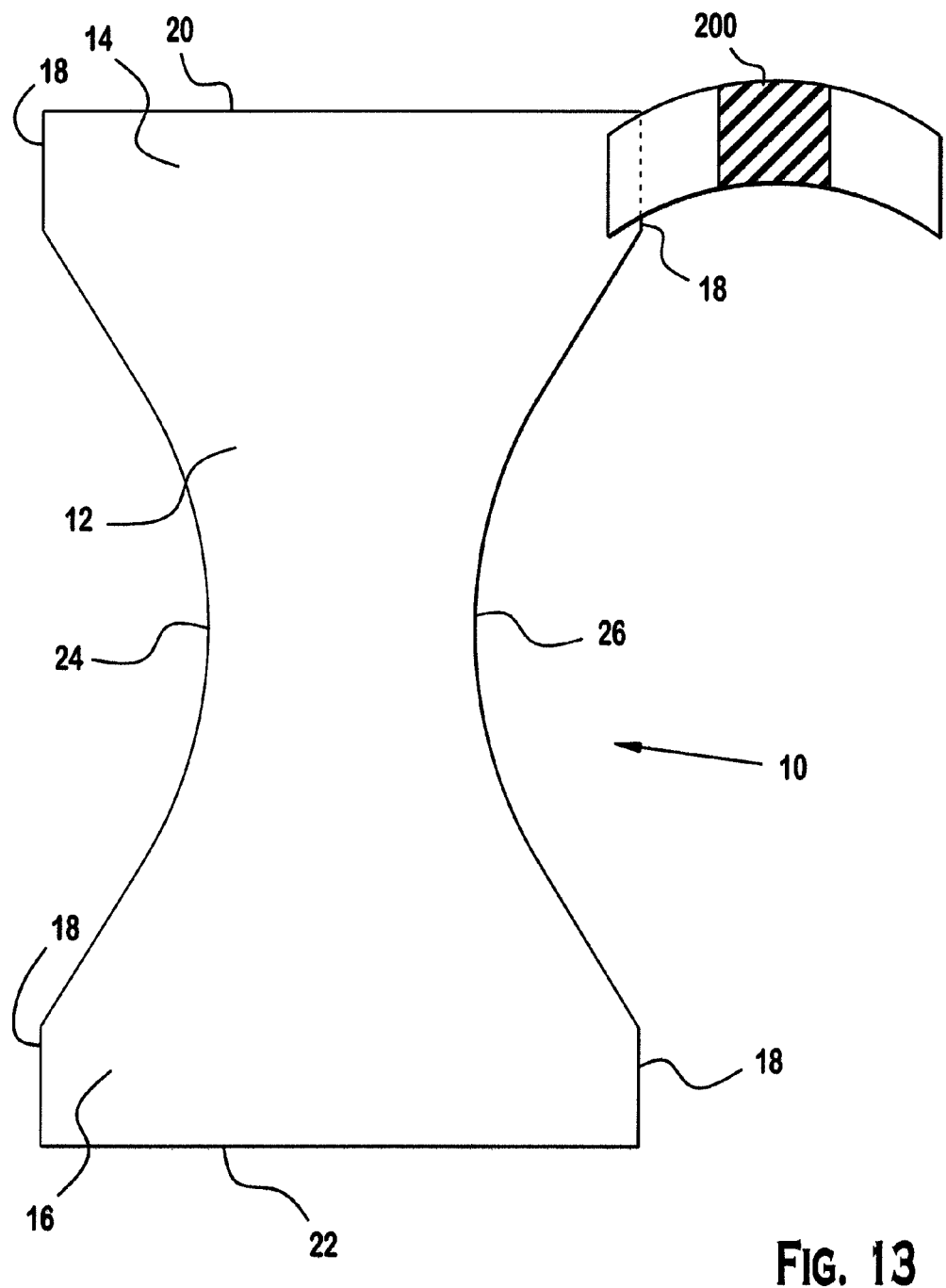
FIG. 13 is a top plan view of an absorbent article having side panels with elastics according to the present invention.
Figure 14:
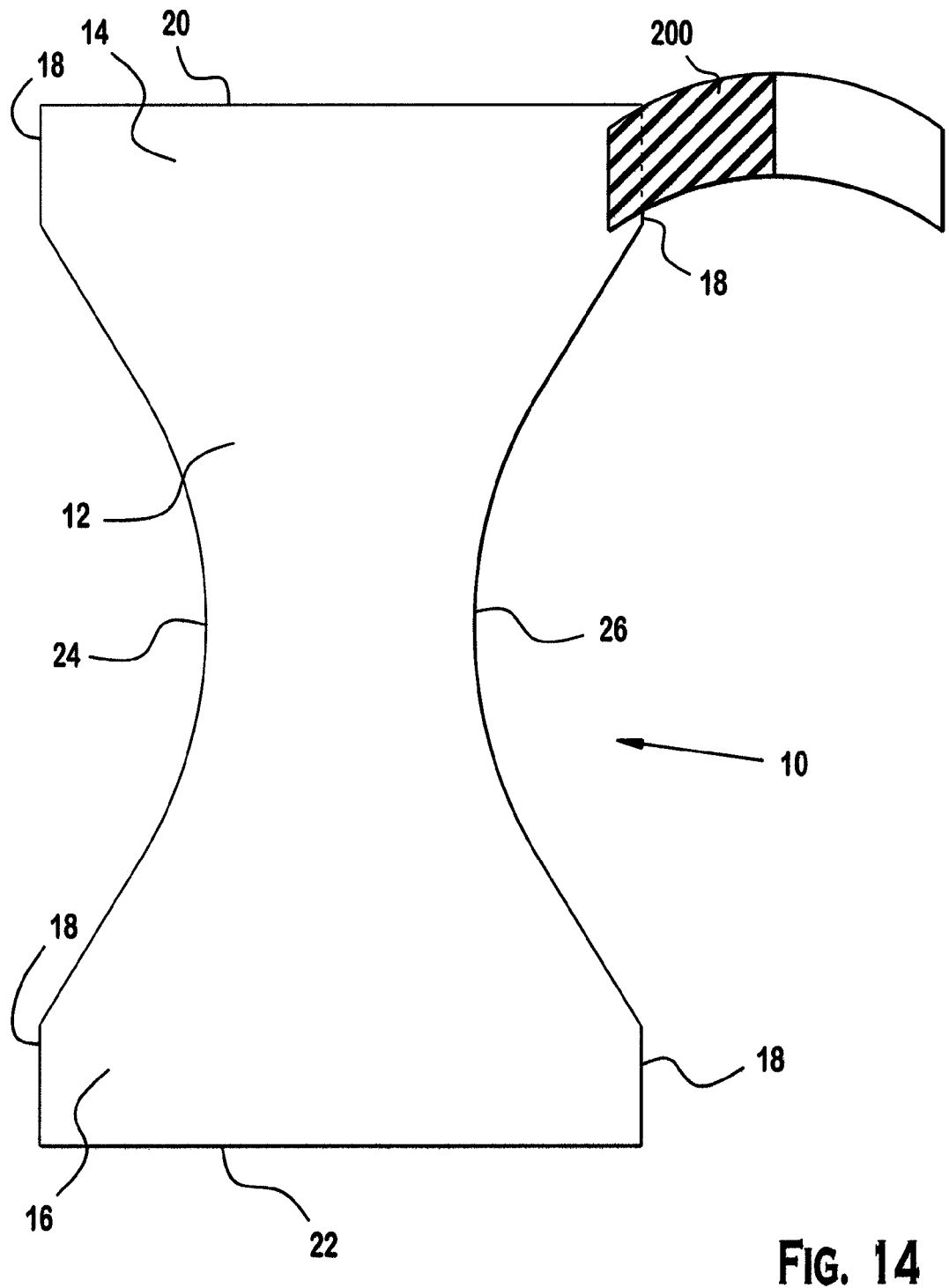
FIG. 14 is a top plan view of an absorbent article having side panels with elastics according to the present invention.
Figure 15:
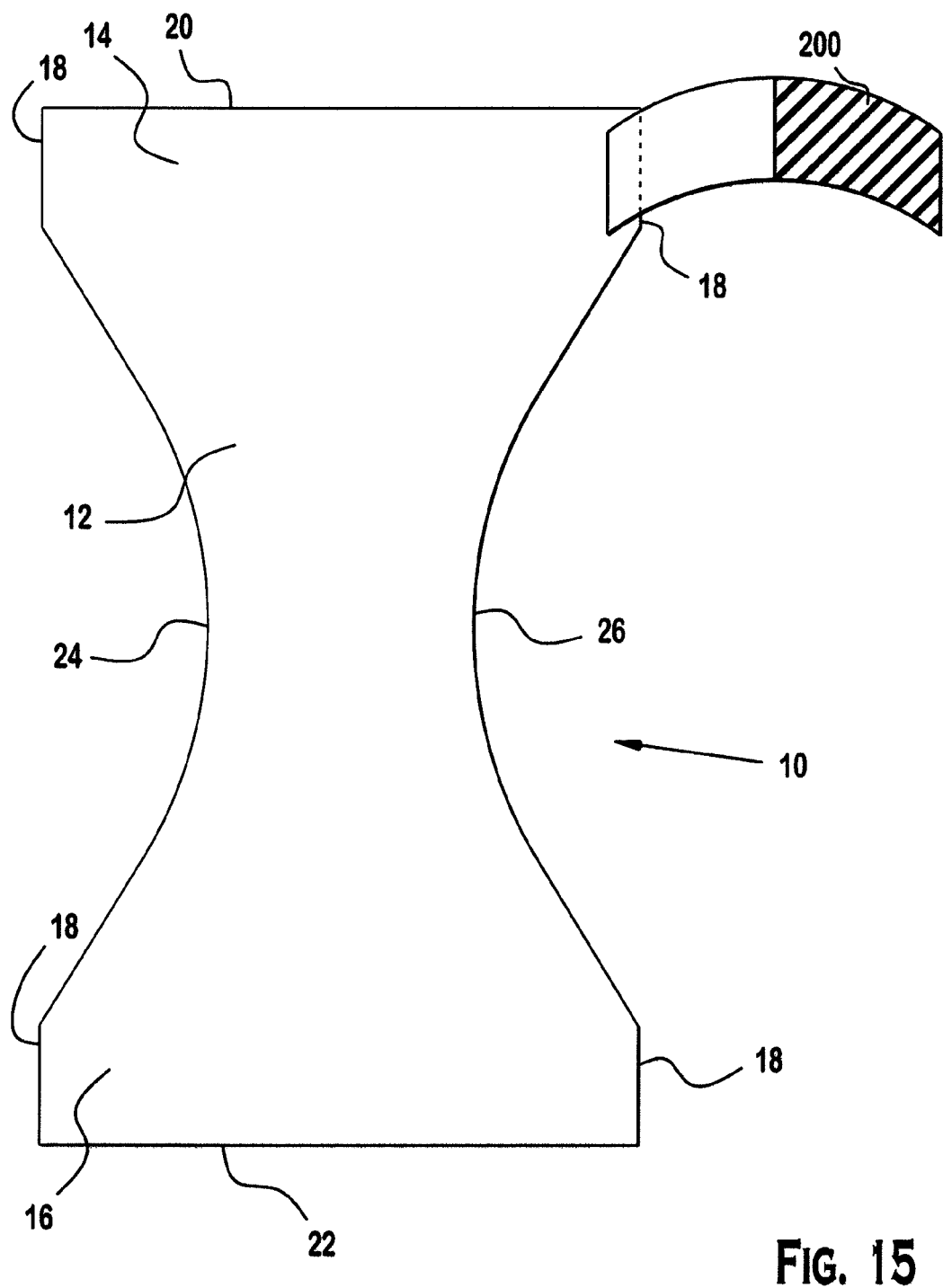
FIG. 15 is a top plan view of an absorbent article having side panels with elastics according to the present invention.

With reference to FIGS. 13-15, any of the side panels described above in the absorbent article 10 may include an elastic portion 200 at different locations on the side panel. With reference to FIG. 13, the elastic portion 200 is shown at a central location. With reference to FIG. 14, the elastic portion 200 is shown at a proximal location. With reference to FIG. 15, the elastic portion 200 may be provided at a distal location. However, it should be understood that one or more elastic portions may be provided in any size and at any location on the side panel according to application and design preference. Optionally the whole side panels may be made of elastic material. Preferably, the elastic material in the side panels has an elastic elongation of 20% to 250%, measured according to the elastic elongation test method, described below. This allows the securing mechanism of the side panels to securely fastened more easily.

Figure 1:
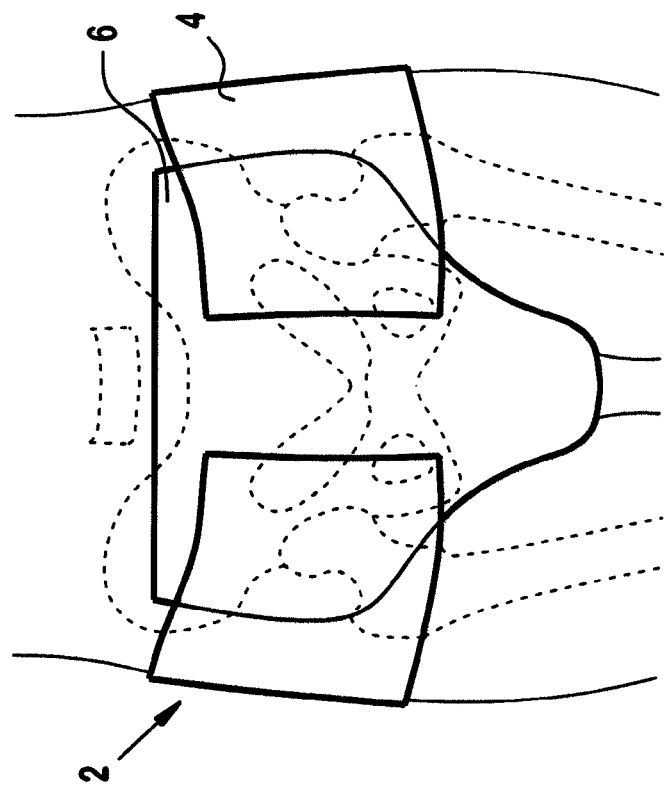
FIG. 1 is a front elevational view of an absorbent article according to the prior art.

The elastic elongation test method measures the behavior of an elastic material at repeated load and unload cycles. The sample is tested in the x-direction according to FIG. 1. The sample is stretched to a predetermined elongation and a cyclic movement between 0 and said predetermined elongation is performed. Desired load and unload forces are recorded. The permanent, i.e., remaining, elongation of the relaxed material is measured.

The permanent elongation after relaxation should be less than 10% and is measured by the method below. Thus an elastic elongation of 30% is defined as that the laminate should have a permanent relaxation after elongation of less than 10% after being exerted to an elongation of 30% in the tensile tester below. An elongation of 30% means an elongation to a length that is 30% longer than the initial length of the sample.

A tensile tester, e.g. Lloyd LRX™, able to perform cyclic movements and equipped with a printer/plotter or software presentation is used. The sample is prepared by cutting it to a width of 25 mm. The length and width of the sample may vary according to the available amount of material. If the material to be tested has a width higher than 25 mm the sample should be cut so that the width is 25 mm. If however the material to be tested, e.g., the elastic material, has a width that is smaller than 25 mm the sample should have the width of the available material piece. The forces then have to be adjusted to the width of the sample according to the values given in brackets in the test method.

The tensile tester is calibrated according to the apparatus instructions. The parameters needed for the test (load and unload forces) are adjusted to:

Crosshead speed: 500 mm/min
Clamp distance: adapted to the length of the test sample
Preload: 0.05 N (0.02 N/10 mm width)

The sample is placed in the clamps and it is made sure that the sample is centered and fastened perpendicularly in the clamps. Depending on the length of the sample the distance between the clamps may vary. If a sample is longer than 100 mm it should be cut to a length of 100 mm. A suitable distance between the clamps is in this case 50 mm. For shorter samples, the distance between the clamps can be shorter then 50 mm but as long as possible. For very short samples, less than 20 mm, the elastic sample should at both ends still be attached to inelastic material of the belt member or side panels, wherein the inelastic material is fastened in the clamps with the elastic part of the sample extending between the clamps. It is in this case important that the entire elastic part of such a sample is located between the clamps.

The tensile tester is started and two cycles between 0 and the predetermined elongation are performed. The crosshead should return immediately and not be held in the stretched position. There should not be any delay between the two cycles of the test method. After the last cycle, the sample is relaxed for 1 minute, then the permanent elongation is measured by stretching the sample until a force of 0.1 N (0.04 N/10 mm width) is detected and the elongation is read.

It should be noted that, while the term "absorbent article" has been used particularly in conjunction with incontinence, and particularly adult incontinence, the invention is not limited to this particular use or any particular size or type of absorbent article implied thereby. The above-described article and method could be used with baby's or children's diapers.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. An absorbent article, comprising:
    a first end, a second end, and an absorbent section therebetween, the first end having longitudinal side edges and a first waist line edge; and
    a pair of side panels extending from longitudinal side edges of said first end of the absorbent article, said side panels fixedly secured to or integral with said longitudinal side edges of said first end of the absorbent article;
    wherein said side panels are made from a single panel of an arc-like shape so as to extend beyond the first waist line edge of the first end of the absorbent article, and having a longitudinal extent so that the side panels are configured to be secured above hip joints of the user and a lower edge of the side panels being configured to be located above the hip joints.

2. The absorbent article of claim 1, wherein the longitudinal extent of the side panels from the first waist line edge to a distal end is between about 3-15% of the longitudinal extent of the article.

3. The absorbent article of claim 1, wherein a longitudinal extent of the article is about between 700 mm to about 1800 mm and the longitudinal extent of the side panels from the first waist line edge to a distal end of the side panel is between about 21 mm to about 270 mm.

4. The absorbent article of claim 1, wherein a longitudinal extent of the article is about between 200 mm to about 500 mm and the longitudinal extent of the side panels from the first waist line edge to a distal end of the side panel is between about 6 mm to about 75 mm.

5. The absorbent article of claim 1, wherein the side panels include a first edge, said first edge extending beyond the first waist edge line, wherein an angle between a line drawn tangent to the first edge and a line extending along the first waist line edge ranges between about 10-90°.

6. The absorbent article of claim 5, wherein the angle ranges between about 30-90°.

7. The absorbent article of claim 5, wherein the angle ranges between about 35-55°.

8. The absorbent article of claim 1, Wherein a longitudinal length of said side panels L3 range between about 12-20% of a longitudinal extent of the article and a transverse width of said side panels range between about 10-30% of the longitudinal extent of the article.

9. The absorbent article of claim 1, wherein a longitudinal extent of the article is about between 700 mm to about 1800 mm, said side panels having a longitudinal length ranging between about 84 mm and 360 mm and a transverse width ranging between about 70 mm and 540 mm.

10. The absorbent article of claim 1, wherein a longitudinal extent of the article is about between 200 mm to about 500 mm, said side panels having a longitudinal length ranging between about 24 mm and 100 mm and a transverse width ranging between about 20 mm and 150 mm.

11. The absorbent article of claim 1, wherein said side panels include an elastic portion, said elastic portion having an elastic elongation of 20% to 250%.

12. The absorbent article of claim 1, further including a fastening device on each said panel, said fastening device having a width of between about 25 mm to about 50 mm, and a length that is 60% of a longitudinal length of the side panels.

13. The absorbent article of claim 1, wherein said side panels include two rectangular-shaped tab portions at each distal end such that the arc-like shaped portion is located between the two rectangular-shaped tab portions, the tab portions and the arc shaped portion having substantially a same thickness in a direction of a longitudinal expansion of the absorbent article.

14. The absorbent article of claim 1, wherein each of the side panels includes an elastic portion and a non-elastic portion, the elastic portion being located away from the longitudinal side edge of the first end of the absorbent article.

15. An absorbent article, comprising:
    a first end, a second end, and an absorbent section therebetween, the first end having longitudinal side edges and a first waist line edge: and
    a pair of side panels extending from longitudinal side edges of said first end of the absorbent article, said side panels fixedly secured to or integral with said longitudinal side edges of said first end of the absorbent article, the side panels made from a single panel of an arc-like shape;
    wherein said side panels include as first edge, said first edge extending beyond the first waist edge line and the side panels are configured to be located above hip joints,
    wherein an angle between a line drawn tangent to the first edge and a line extending along the first waist line edge ranges between about 10-90°.

16. The absorbent article of claim 15, wherein the longitudinal extent of the side panels from the first waist line edge to a distal end is between about 3-15% of the longitudinal extent of the article.

17. The absorbent article of claim 15, wherein a longitudinal extent of the article is about between 700 mm to about 1800 mm and the longitudinal extent of the side panels from the first waist line edge to a distal end of the side panel is between about 21 mm to about 270 mm.

18. The absorbent article of claim 15, wherein as longitudinal extent of the article is about between 200 mm to about 500 mm and the longitudinal extent of the side panels from the first waist line edge to a distal end of the side panel is between about 6 mm to about 75 mm.

19. The absorbent article of claim 15, wherein the angle ranges between about 30-90°.

20. The absorbent article of claim 15, wherein, the angle ranges between about 35-55°.

21. The absorbent article of claim 15, wherein a longitudinal length of said side panels L3 range between about 12-20% of a longitudinal extent of the article and a transverse width of said side panels range between about 10-30% of the longitudinal extent of the article.

22. The absorbent article of claim 15, wherein a longitudinal extent of the article is about between 700 mm to about 1800 mm, said side panels having a longitudinal length ranging between about 84 mm and 360 mm and a transverse width ranging between about 70 mm and 540 mm.

23. The absorbent article of claim 15, wherein a longitudinal extent of the article is about between 200 mm to about 500 mm, said side panels having a longitudinal length ranging between about 24 mm and 100 mm and a transverse width ranging between about 20 mm. and 150 mm.

24. The absorbent article of claim 15, wherein said side panels include an elastic portion, said elastic portion having an elastic elongation of 20% to 250%.

25. The absorbent article of claim 15, further including a fastening device on each said panel, said fastening device having a width of between about 25 mm to about 50 mm, and a length that is 60% of a longitudinal length of the side panels.

26. The absorbent article of claim 15, wherein said side panels include two rectangular-shaped tab portions at each distal end such that the arc-like shaped portion is located between the two rectangular-shaped tab portions, the tab portions and the arc-shaped portion having substantially a same thickness in a direction of a longitudinal expansion of the absorbent article.

27. The absorbent article of claim 15, wherein said side panels includes an elastic portion and a non-elastic portion, the elastic portion being located away from the longitudinal side edge of the first end of the absorbent article.

* * * * *